US012582547B2

(12) United States Patent
Paul

(10) Patent No.: US 12,582,547 B2
(45) Date of Patent: Mar. 24, 2026

(54) HANDHELD PALM COOLING DEVICE

(71) Applicant: Ariel Jeremy Paul, Boulder, CO (US)

(72) Inventor: Ariel Jeremy Paul, Boulder, CO (US)

(73) Assignee: Apex Cool Labs, Inc., Boulder, CO (US)

( * ) Notice: Subject to any disclaimer, the term of this patent is extended or adjusted under 35 U.S.C. 154(b) by 261 days.

(21) Appl. No.: 18/128,163

(22) Filed: Mar. 29, 2023

(65) Prior Publication Data

US 2025/0041105 A1 Feb. 6, 2025

(51) Int. Cl.
    *A61F 7/00* (2006.01)
(52) U.S. Cl.
    CPC .... *A61F 7/0085* (2013.01); *A61F 2007/0056* (2013.01); *A61F 2007/0057* (2013.01)
(58) Field of Classification Search
    CPC ................ A61F 7/03; A61F 2007/0036; A61F 2007/0087
    See application file for complete search history.

(56) References Cited

U.S. PATENT DOCUMENTS

| | | | | |
|---|---|---|---|---|
| 5,269,369 A | * | 12/1993 | Faghri | ................ A41D 13/0056 607/104 |
| 6,074,414 A | * | 6/2000 | Haas | ......................... A61F 7/02 607/108 |
| 2016/0008164 A1 | * | 1/2016 | Anderson | ............. A61F 7/0053 607/104 |
| 2023/0045204 A1 | * | 2/2023 | Henzler | ................. A61F 7/007 |

* cited by examiner

*Primary Examiner* — Kaitlyn E Smith

(57) ABSTRACT

Muscles held under tension undergo a chemical reaction that generates heat within the muscle, and subsequently that heat contributes to muscle fatigue. Research in the field of physiology and sports medicine has demonstrated that actively cooling an athlete's core body temperature can rapidly rejuvenate a fatigued muscle thereby allowing the athlete to extend the muscle's potential. Mammalians have several areas of glabrous tissue wherein a dense network of veins near the surface of the skin act as heat exchangers for cooling and regulating their core temperature. The process for effective cooling via glabrous tissue is optimized within a narrow range of temperatures. Presented herein is a handheld cooling device which is optimized for the efficient transfer of heat away from the fatigued muscles via direct contact with glabrous tissue.

15 Claims, 11 Drawing Sheets

100

101

102

104

106

112

124

132

136

Time (minutes) .vs. Temperature inside the Reservoir 104
106
118
118
118

138

100

200

120    120

102

210

120    120

102

300

305

310

315

300

330

305

315

330

325   310

HANDHELD PALM COOLING DEVICE

TECHNICAL FIELD

This disclosure is related to the field of sports medicine and physiology, and more specifically, the thermal regulation of humans through glabrous tissues for the purpose of increased athletic performance.

BACKGROUND OF THE DISCLOSURE

It is well understood that during the course of a workout muscles will fatigue to a point where performance is reduced, and continued efforts to push beyond that point can lead to exhaustion where the muscles simply cannot complete one more repetition or another mile. Muscles under tension will convert stored energy into heat through a chemical reaction, causing the body to heat up. An enzyme essential to complete the chemical reaction is named muscle pyruvate kinases (MPK). Researchers have found that this enzyme is active at cooler temperatures, and that as the muscle or body heat up, the enzyme deforms and enters an inactive state. The enzyme can be returned to an active state by cooling the fatigued muscles, which in-turn resets or extends the muscles potential. In addition to localized muscular fatigue, during the course of a workout or intense activity, core body temperature can also rise, further impeding the ability to perform. Core body temperature is also well correlated to heart rate, so lowering core body temperature from an elevated state also accelerates heart rate recovery.

Presented herein are various embodiments of a portable cooling device which may be utilized by athletes across multiple sports to reduce heat-related muscle fatigue and improve recovery. The embodiments presented are primarily designed to be in direct physical contact with mammalian glabrous skin surfaces or tissue—an area of the body where a dense vascular network facilitates rapid heat loss. Humans have multiple locations containing glabrous skin surfaces including, but not limited to, the palms of the hands and soles of the feet, as well as areas of the face and ears.

The vascular network residing in the glabrous tissue, known as AVAs or arteriovenous anastomoses, aid in body temperature regulation by rapid cooling with highly variable blood flow dependent upon temperature. When the glabrous tissue is exposed to extreme coolness, such as an ice bath, the AVAs restrict blood flow by means of vasoconstriction, thereby limiting the heat exchange to the core of the body. In contrast, during exercise or hot weather, as much as 60 percent of the total cardiac output may pass through the network—thereby facilitating core cooling.

The device and methods of use presented herein provide means for a highly efficient transfer of heat from the glabrous tissue of an individual via heat pipes in contact with a working fluid contained in an insulated thermal reservoir, wherein the reservoir fluid is maintained at a constant temperature via an encapsulated phase change material of suitable properties.

The device is intended to aid thermoregulation of individuals under multiple circumstances. The working temperature of the thermal reservoir is chosen to optimize the temperature of the heat pipe surface in contact with the glabrous tissue to avoid vasoconstriction or injurious temperatures while allowing maximized heat transfer. In a cooling condition, the encapsulated phase change material is frozen before use, and combined with a working fluid that can contact the heat pipes.

In the preferred embodiment, the device is intended to provide means to contact with glabrous tissue in the palms for the purpose of cooling the palms. An alternative use of the preferred embodiment exists wherein the device can be used to warm the palms if the thermal reservoir is filled with a warm fluid. Alternative embodiments are presented which may also be applied to other portions of the body, including the soles of the feet or areas of the face which comprise glabrous skin (such as the upper cheeks).

BRIEF DESCRIPTION OF THE DRAWINGS

To facilitate a fuller understanding of the present disclosure, reference is now made to the accompanying drawings, in which like elements are referenced with like numerals. These drawings should not be construed as limiting the present disclosure but are intended to be illustrative only.

DETAILED DESCRIPTION OF EMBODIMENTS

This disclosure provides detailed descriptions of inventive concepts which are applicable, but not limited to, a handheld cooling device. The device and methods of use presented herein provide means for a highly efficient transfer of heat from the glabrous tissue of an individual via heat pipes in contact with a working fluid contained in an insulated thermal reservoir, wherein the fluid contained within a reservoir is maintained at a controlled temperature. Further disclosed are various embodiments and methods for maintaining a proper temperature (roughly 44 F to 60 F) necessary to avoid vasoconstriction and facilitate the heat transfer from the glabrous tissue. The disclosure and descriptions herein correspond to the figures accompanying this specification.

Figure 1:
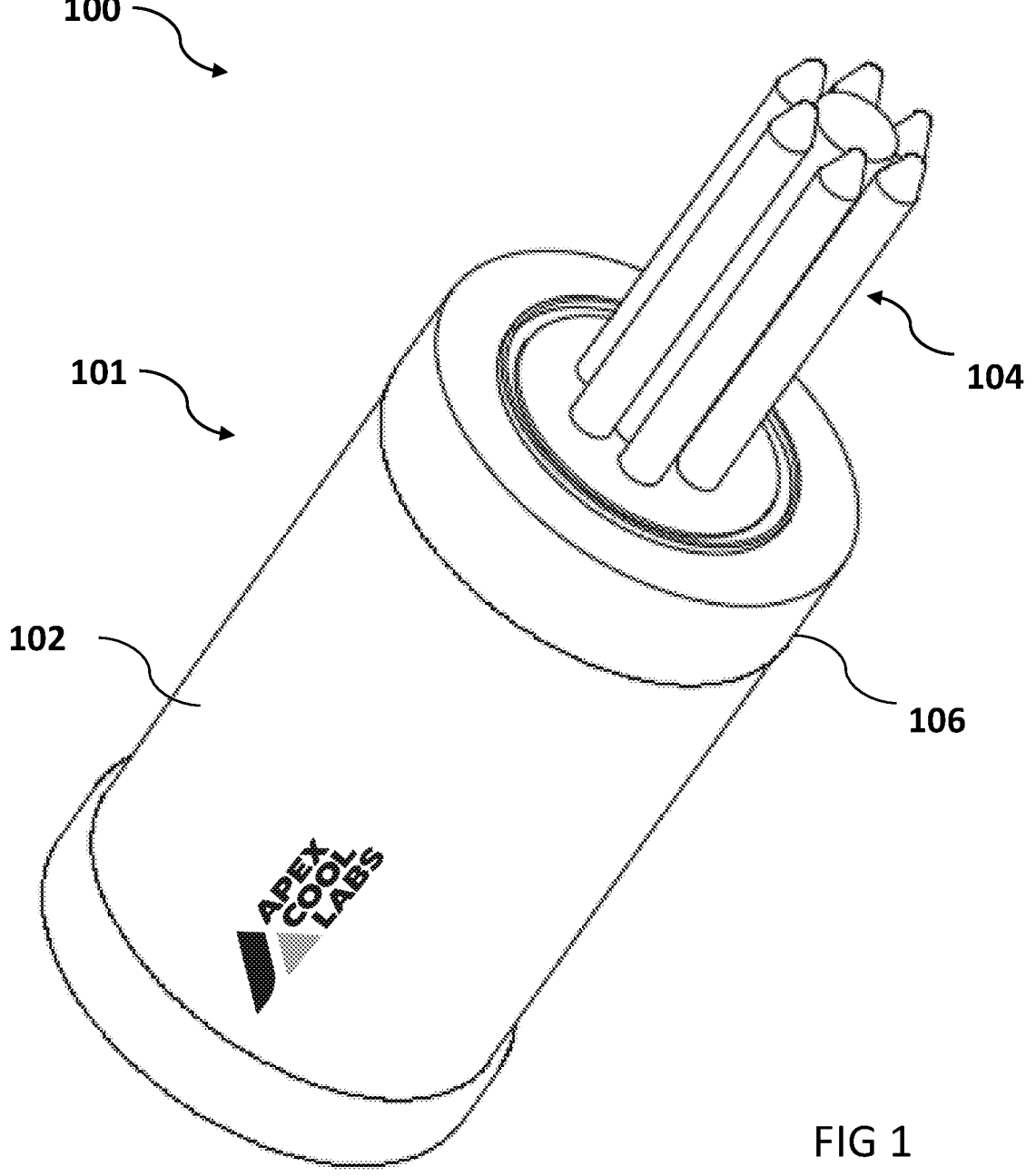
FIG. 1 shows an isometric view of the handheld palm cooling device corresponding to an embodiment of the present disclosure.

FIG. 1, shows an upper isometric view of the assembled palm cooling device 100 and deconstructs the palm cooling device 100 into several functional components. The first component is the vessel body 102 which encompasses an internal cavity or reservoir capable of containing liquids. The second component is the vessel lid 106 which mates to the vessel 102 to form a fully enclosed reservoir which is leak-proof, or water-tight seal within the vessel. The lid also provides a mechanical seat and pass-through for the third component, the heat exchange assembly 104. Collectively, the vessel body 102 and the vessel lid 106 in combination compose the vessel 101.

A portion of the heat exchange assembly 104 resides within the vessel 101 and a portion of the heat exchange assembly exists external to the vessel. The details of the heat exchange assembly are presented in detail within this specification, but the general function of the heat exchange assembly is to facilitate the transfer of heat between the external surfaces of the heat exchange assembly visible in FIG. 1 and the surfaces of the heat exchange assembly residing within the vessel 101.

It should be understood that throughout this disclosure a target or desired temperature of the fluid within the vessel's reservoir may be greater-than or less-than the external temperature. In the preferred embodiment, the fluid temperature within the vessel would be cooler than the temperatures external to the vessel—thereby facilitating the cooling of the external surfaces of the heat exchanger assembly. In alternative embodiments, the temperature of the fluids within the vessel may be warmer than the temperatures external to the vessel—thereby facilitating the heating of the external surfaces of the heat exchanger. As multiple embodiments and conditions may exist, for the purpose of this disclosure, concepts of heat transfer or the flow of heat is presented simply as being the movement of heat energy in either direction (i.e. hot-to-cold or cold-to-hot) in order to reach a thermal equilibrium.

Figure 2:
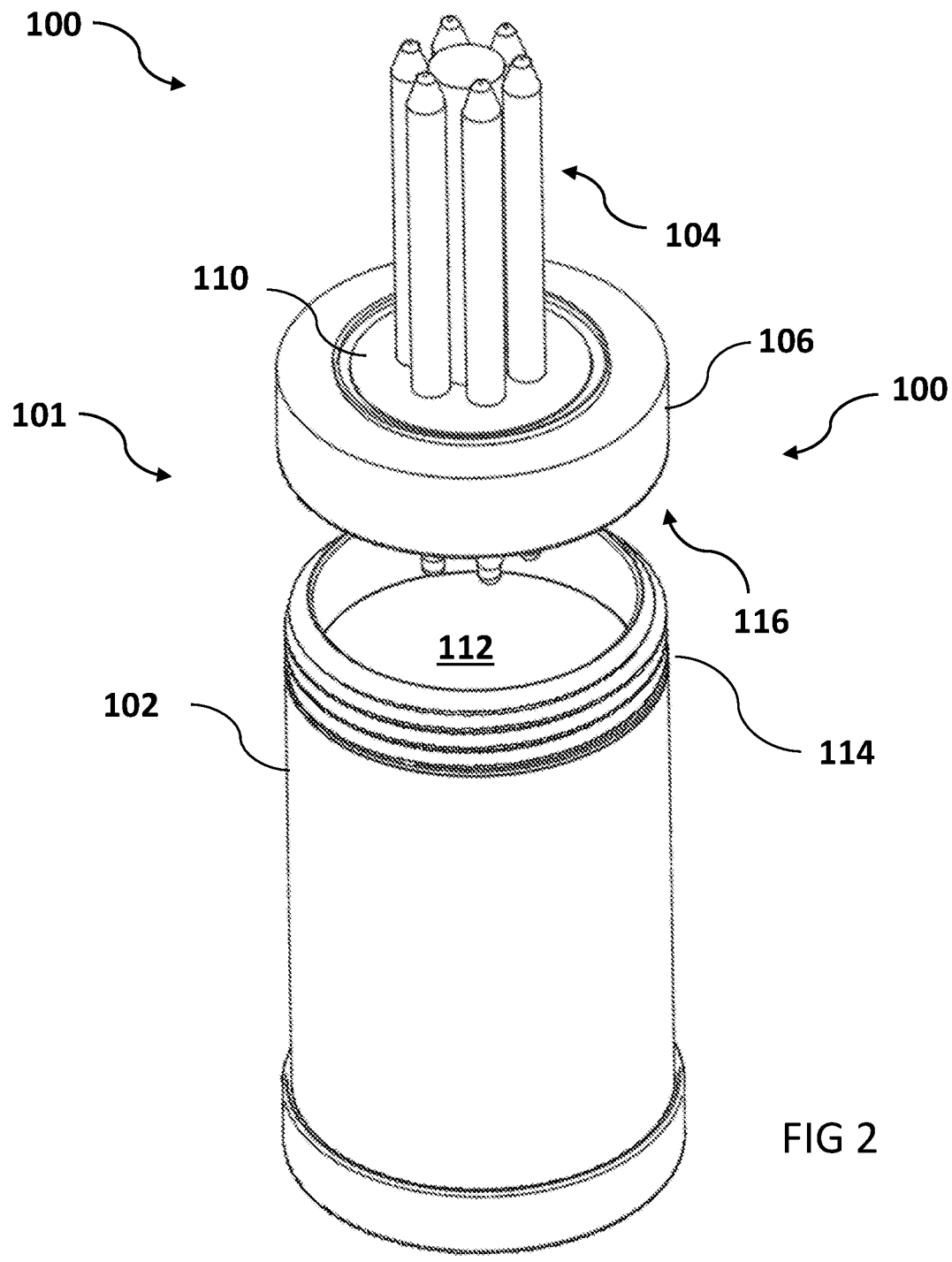
FIG. 2 shows a downward isometric view of the handheld palm cooling device in the open state with views of the internal vessel cavity corresponding to an embodiment of the present disclosure.

Moving to second figure, FIG. 2, the palm cooling device 100 is shown in an open state, wherein the vessel body 102 is separated from the vessel lid 106 and the heat exchange assembly 104. The vessel body has an inner cavity capable of holding liquids which functions as, and is hereby known, a reservoir 112 irrespective of the presence of liquids. A mating connection exists surrounding the perimeter of the opening or port between the vessel body 102 and the vessel lid 104. In the open condition, the opening allows access to the inner cavity or reservoir 112 such that materials, including liquids, solids, or gases, may be placed within the reservoir. The mating connection is shown in the figure with the lid having a lid flange 116 and the vessel body having a vessel flange 114. In the preferred embodiment, in the closed position, the mating connection is water-tight or leak-proof. In some embodiments the connection may be a screw or threaded type flange, or it may be a friction-fit type flange. The connection may or may not include a gasket, special coating, or other common methods to improve the quality of a seal. In some embodiments, the opening or port may reside anywhere on the vessel traversing the vessel wall between the exterior surface of the vessel and the inner cavity or reservoir 112.

The vessel lid 106 includes a mechanical pass-thru or grommet 110 which provides a mechanical attachment and a support for the heat exchange assembly 104. In addition to providing mechanical structure, in some embodiments the grommet 110 also adds additional thermal isolation between the areas external to the ambient temperatures external to the handheld cooling device 100 and the temperatures within the reservoir 112 when the vessel 101 is in the closed condition. The grommet surrounds elements of the heat exchange assembly to form a water-tight or leakproof seal between the inner reservoir 112 and points external to the vessel 101.

In the preferred embodiment, the vessel 101 is of sufficient dimensions and capacity to allow the device to maintain a target temperature within the reservoir 112 and enable operation (e.g., an active state of palm cooling or passive state of storage), for extended periods of time under a multitude of ambient environmental conditions. The reservoir is constructed in a manner to provide sufficient insulation and be resistant to wear and damage.

In one embodiment, a double-wall vacuum insulated stainless steel thermos may be used as the vessel 101. This sort of thermos provides both superior insulation and resistance to damage. Other embodiments for the vessel 101, however, may utilize various containers including those made of other metals, plastic, or a combination therein. The size, form factor, surface, attachments, and other design details of the thermal reservoir could take many forms depending on the application.

Figures 3A, 3B:
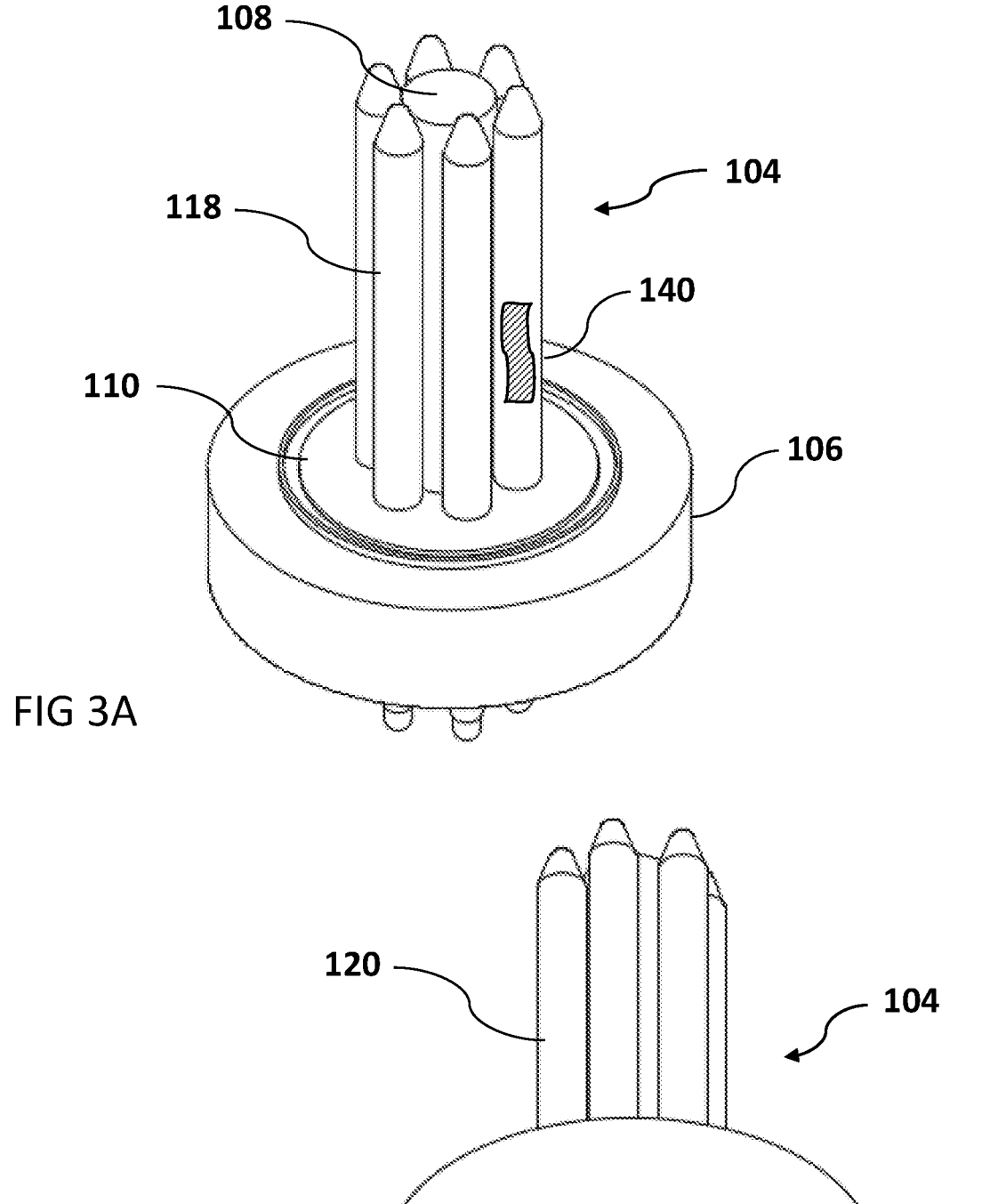
FIG. 3A shows a downward isometric and FIG. 3B shows an upward isometric view of the lid with heat exchangers corresponding to an embodiment of the present disclosure.

FIG. 3A and FIG. 3B show the heat exchanger assembly 104 from a downward and upward perspective respectively. The heat exchanger includes the vessel lid 106 with a threaded lid flange 116—visible in the upward facing perspective encircling the perimeter of the lid. The heat exchange assembly 104 includes a grommet 110 which is the attachment point to the lid 106, a plurality of heat pipes 118 which extend through the grommet 106, and, in the preferred embodiment, a central insulator 108.

To aid in the disclosure, the continuous heat pipe 118 is sectioned and herein reference as the upper heat pipe 120, defined as portion residing external to the vessel and shown above the grommet 110, and the lower heat pipe 122, defined as the portion of the heat pipe 118 configured to reside internal to the vessel and shown below the grommet. To say it another way, the heat pipe has a proximal end residing internal to the cavity of the vessel referred to as the lower heat pipe 122, and a distal end corresponding to the end of the pipe positioned some length external to the vessel referred to as the upper heat pipe 120.

In a theoretical or non-ideal embodiment of the heat exchange assembly 104, a single heat pipe 118 can suffice to achieve the intended function of transferring heat between a reservoir and external surfaces of the heat pipe 118. In a preferential embodiment, it is desirable to have a plurality of heat pipes 118 to increase the contact surface area. Shown in FIG. 3A/B is the preferred embodiment having six heat pipes 118 which creates a balance between functional performance, mechanical requirements, and marketable cost constraints. Embodiments comprising an array between one to eight heat pipes 118 or more per heat exchange assembly 104 do not alter the functional principals presented.

In the preferred embodiment and as shown, the heat exchange assembly 104 consists of an array of heat pipes 118 of suitable dimensions and arrangement to be strong and allow proper thermal contact to the glabrous tissue. As the device is intended to be held within a closed fist, the length of upper heat pipe 120 may be between three and seven inches—with a preferred embodiment length generally around 4 inches. While other thermally conductive materials may be chosen, heat pipes are chosen for their superior thermal conductivity which are generally multiple orders of magnitude greater than an equivalent piece of raw material. In a non-preferred embodiment, however, a solid or hollow pipe of thermal conductive material, such as aluminum, brass, or other metal, may be used as a heat pipe for this application. The heat pipes allow transfer of heat in a continuous and optimized manner between the skin in contact with the device and the fluid within the reservoir with no moving parts. Heat pipes also have a long working life of over 10 years and are commonly constructed of robust materials that are resistant to most types of wear and damage.

There are various constructions of heat pipes which may be used to accomplish the goal of transferring energy from the reservoir to a point external to the vessel. A non-limiting example of heat pipe includes standard heat pipes having an exterior walled envelope, a wick, and a working fluid. Other examples include variable conductance heat pipes, vapor chamber heat pipes, or diode heat pipes.

In one embodiment, the heat pipes are 10 mm in diameter, made of copper, and considered thick-walled. Common classification for defining pipe thickness includes "thick-walled" where the diameter divided by the thickness is less than 20, and "thin-walled" as pipes having a diameter divided by thickness that is greater than 20. Specific to this application, the thick-walled pipe provides additional mass, thermal conductivity, and heat capacitance, so that the wall temperatures do not fluctuate locally when grasped by the user.

Copper is an ideal material given its inherently high thermal conductivity, and the wall thickness provides structural strength to the heat exchange assembly. However, other embodiments may include heat pipes constructed of alternative metals, alloys, or other materials. Common metals which could be used in the construction of heat pipes include various alloys of aluminum and stainless steel, but could also include any material with a thermal conductivity above 10 W/(mK) could be used for their construction (such as titanium, alloys of steel, brass, bronze, thermally conductive plastic, silicon carbide, graphite, etc).

In some embodiments, a nanoceramic coating 140 is applied to the heat pipes 118 to avoid discoloration from oxidation. Multiple different coatings or surface treatments are possible, including epoxy coatings, paints, or various plating processes. Depending on the material used for the heat pipes 118, coatings or surface treatments could be applied to enhance various properties of the heat pipes such as corrosion resistance, thermal conductivity, aesthetic appearance, durability, texture, or chemical resistance.

The array or plurality of heat pipes 118 of the heat exchange assembly 104 is mechanically held in place by the grommet 110 which provides a passage from the area external to the vessel 101 to the reservoir 112 of the vessel. The feedthrough is constructed to provide thermal insulation, structural stability, and resistance to the environment. In some embodiments the grommet may be integral to the wall of the vessel.

In one embodiment, a plurality of heat pipes 118 are glued into the grommet 110 with a thick layer of epoxy that provides additional structural stability, liquid proof sealing, and thermal insulation. The grommet 110 also may include a layer of EPDM foam glued onto the thick epoxy layer using cyanoacrylate glue. Closed-cell EPDM foam is chosen for its insulation properties as well as its superior resistance to environmental conditions such as moisture and UV exposure. Cyanoacrylate glue is used to adhere the EPDM to the epoxy layer as it is one of the few adhesives effective on EPDM foam.

In the preferred embodiment, a central insulating rod 108 of closed cell neoprene foam is used in the interior of the heat pipe array to provide further insulation and enhanced structural stability to the heat pipe assembly 104. The central insulating rod can be held in place by friction fit between the heat pipes, glued to the EPDM foam with cyanoacrylate glue, or a combination therein. Closed cell neoprene foam is a preferred material for the central insulating rod due to its excellent insulation properties and resistance to environmental factors.

The grommet 110 could come in many alternate forms, including other plastics in which the heat pipe 118 are attached (e.g. by adhesives, mechanical connection, etc.) directly to the plastic, or included during the plastic molding process. The heat pipes 118 could also be soldered, brazed, welded, or glued to another material such as metal existing as a section of the grommet 110. In other embodiments, the grommet may exist as an integral or non-removal portion of the thermal reservoir, wherein an orifice to fill the reservoir may reside elsewhere.

Figure 4:
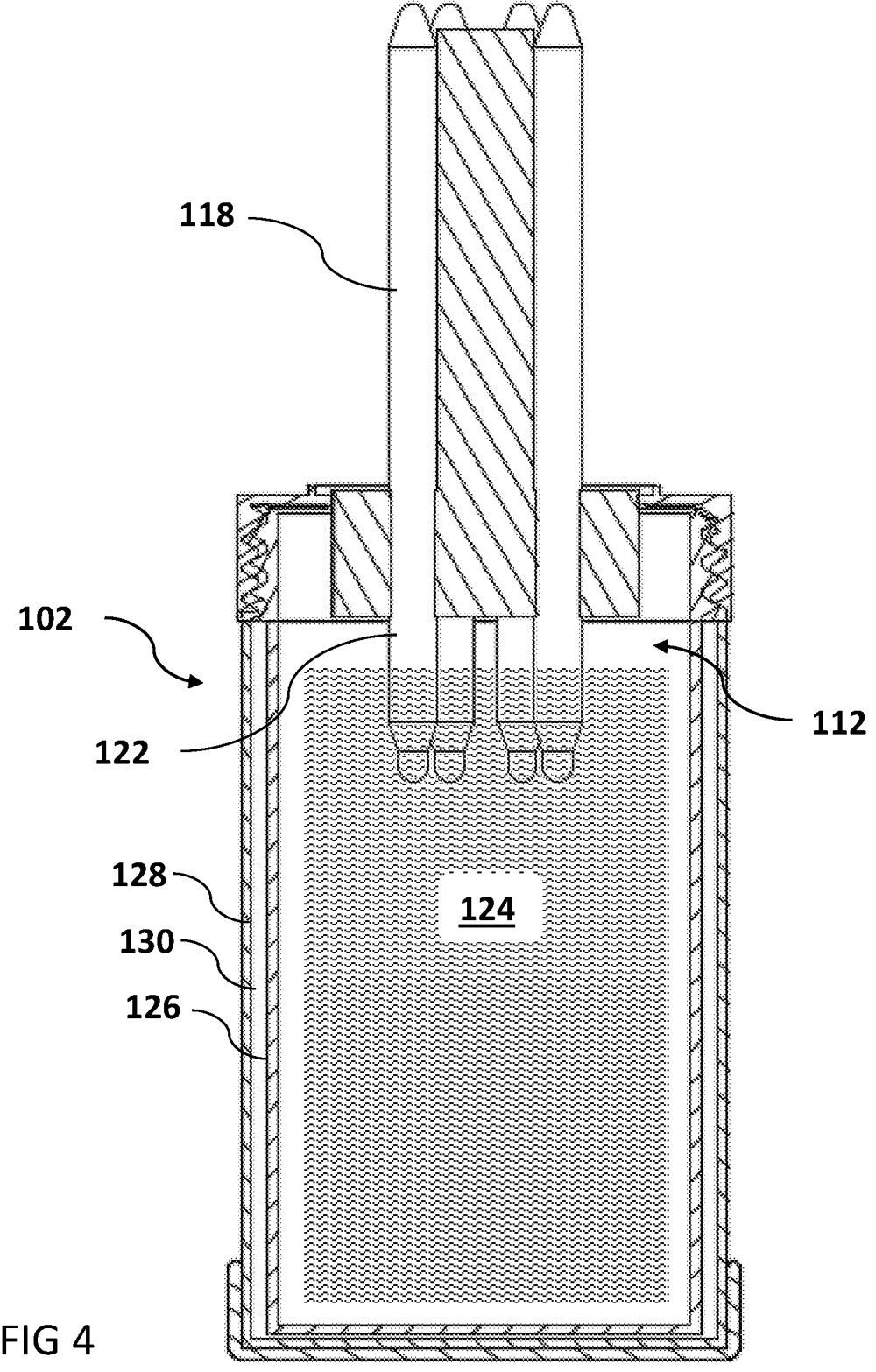
FIG. 4 shows the vessel filled with a medium corresponding to an embodiment of the present disclosure.

A sectional view of the handheld palm cooling device in the closed position is shown in FIG. 4. The cross section allows illustration of the vessel walls of the preferred embodiment, wherein the vessel body 102 is constructed of an outer vessel wall 128, an air gap 130, and an inner wall 126. In a preferred embodiment, the air gap 130 comprises a vacuum or area of low-pressure relative to the ambient pressure. In other embodiments, the air gap may additionally include a variety of other insulating materials.

The collective sum of the thermal energy existing in the reservoir 112 is herein referred to as the thermal ballast. In the preferred embodiment, the thermal ballast acts as a heat sink by absorbing heat from the upper heat pipe. For the purpose of simplifying concepts of heat transfer within this disclosure, the vessel is presented to be ideally insulated with heat transfer limited to the heat pipes, and individual elements existing within the reservoir have uniform thermal gradient.

The reservoir 112 of the vessel shown in FIG. 4 includes a working fluid 124 which is at least partially in contact with the lower heat pipe 122. The working fluid 124 allows efficient transfer of heat between the heat pipes 118 and the reservoir 112. The working fluid 124 has a mass and temperature which are included as a portion of the thermal ballast used to maintain the reservoir target temperature of the device. In some embodiments, such as that shown in FIG. 4, the working fluid 124 constitutes the majority of the thermal mass within the reservoir 112, albeit the mass of any empty space and that of the lower heat pipes 122.

In the preferred embodiment, water is used as the working fluid 124, due to relatively high thermal conductivity, very large specific heat, and nontoxic nature. Many other fluids could occupy the thermal reservoir 112, whether aqueous solutions of various chemicals, colloidal mixtures, or pure elements. For instance, mercury would be an ideal working fluid due to its excellent thermal conductivity and high specific heat but would be impractical due to its expense and toxicity. In an embodiment constructed as a closed system, however, a more exotic working fluid could be utilized, especially if the chance of exposure was eliminated.

An additional embodiment exists where the reservoir 112 is initially filled with a homogeneous solid form of the working fluid 124 which changes phase into a liquid as it heats up.

Figure 5:
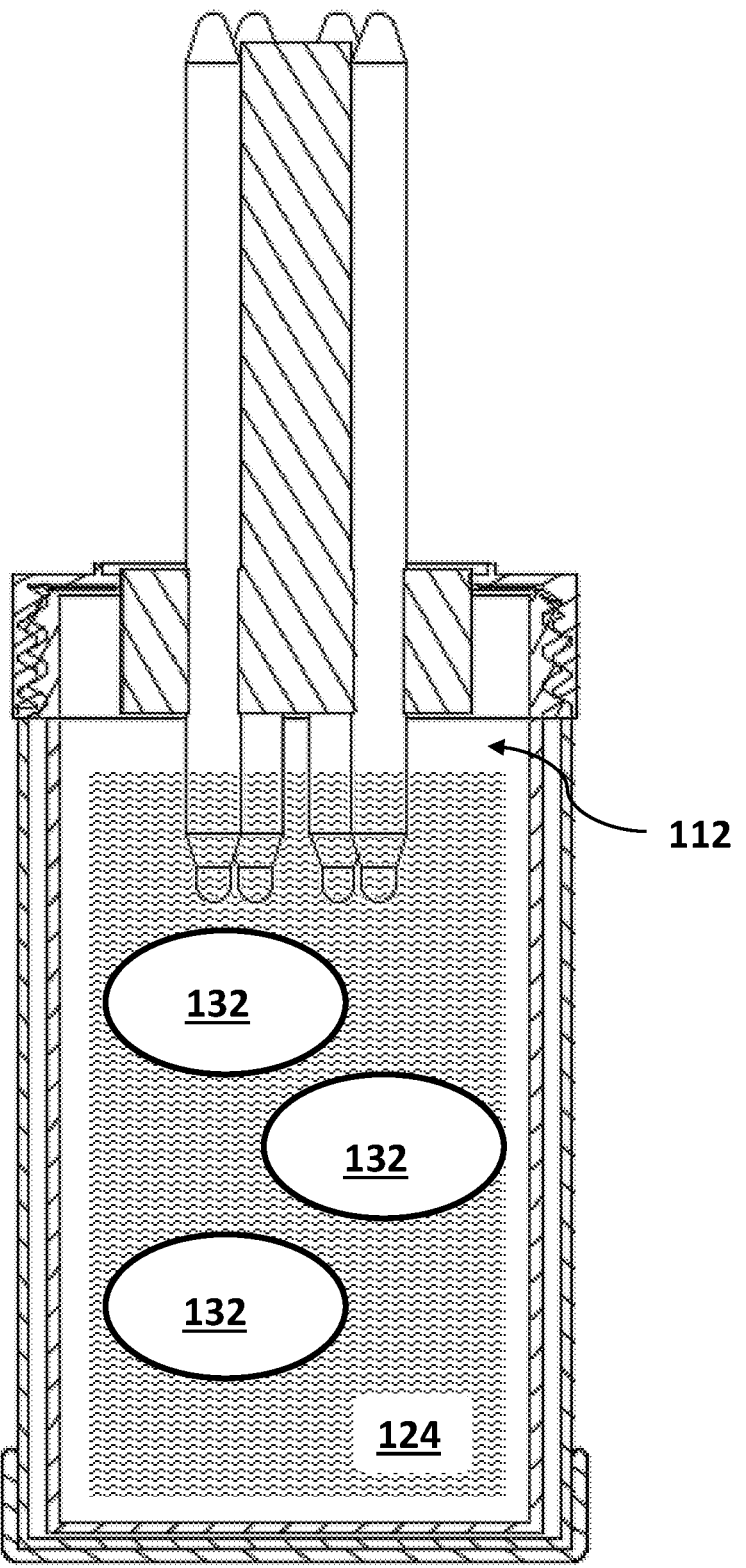
FIG. 5 shows the vessel filled with a plurality of mediums corresponding to an embodiment of the present disclosure.

The embodiment presented in FIG. 5 shows the addition of secondary element 132 into working fluid 124 within the reservoir 112 to create a non-homogeneous thermal ballast. In this embodiment, the temperature of the working fluid 124 is maintained primarily via thermal interaction with the secondary element 132.

In some simple embodiments, the secondary element can comprise an alternate phase of the working fluid 124—such as where the secondary element being ice in a working fluid of water. In other simple embodiments, the secondary element can simply be a solid mass at a different temperature with a given specific heat. In such cases, the thermal interaction and controls can still vary depending upon a myriad of factors including the starting temperature of the secondary element, surface area, mass, and in the case of ice, phase change thresholds.

In other embodiments, reservoir temperature may be controlled through complex means such as activity inherent to the secondary materials 132 such as via means of a chemical reaction, powered temperature regulation elements, thermoelectric devices, refrigeration or heating elements, expansion or compression of gasses, or heat pumps.

This increased level of control is required for the application of palm cooling for relief of overheated muscles, where the intention is to cool via glabrous surfaces within a tight temperature range. For example, simply creating an ice water bath inside the reservoir 122 would create a situation that is either too cold and causes vasoconstriction in the glabrous skin or lacks the ability for prolonged operation within a reasonable sized reservoir.

Figure 6:
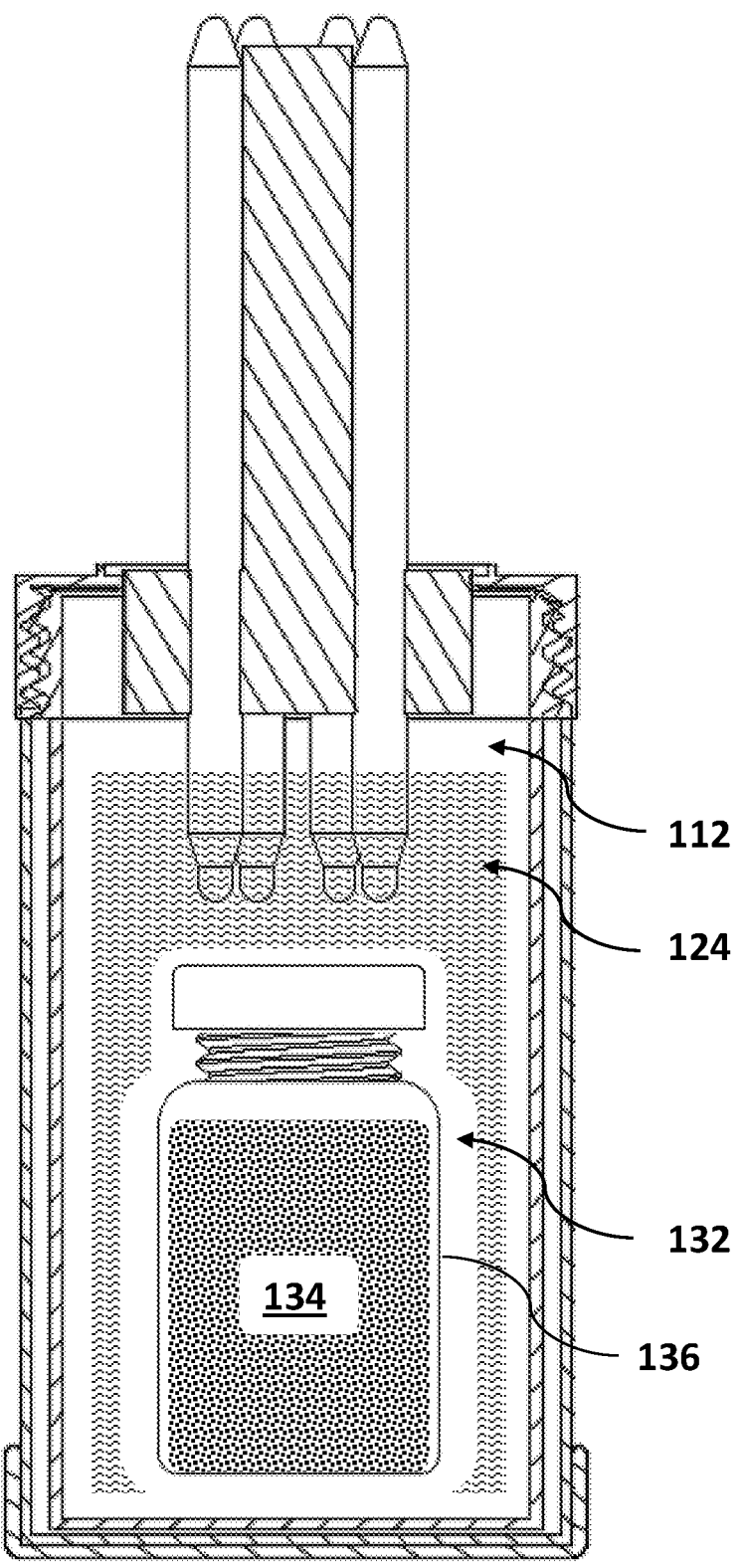
FIG. 6 shows the vessel filled with an isolated medium corresponding to an embodiment of the present disclosure.

The preferred embodiment includes the introduction of secondary matter 132 into a working fluid 124 as shown in FIG. 6, wherein the secondary matter comprises a phase change material 134 encapsulated within a sealed container 136. The encapsulated phase change material is used within the thermal reservoir 112 to provide a bulk of the thermal ballast for maintaining the temperature of the thermal reservoir. This approach gives greater control and predictability of the thermal interaction as the working fluid 124 and the phase material 134 do not mix, and the surface area between sealed container 132 and working fluid remain constant.

Preferences regarding the construction of the sealed container 136 follow. HDPE is chosen for the containing jar for its ability to withstand many freeze thaw cycles and its high abrasion resistance. The lid of the HDPE jar is chosen for convenience and a leakproof seal. The jar and lid are sealed together using an adhesive appropriate for low surface energy polymers.

The phase change material 134 leverages the thermal inertia related to the latent heat of fusion of a material, also known as the heat of melting. When a material melts and changes from its solid to liquid phase, a large amount of energy is required. In general, solids possess a high degree of ordered structure, such as a crystalline lattice. To melt a solid, the solid absorbs energy to disrupt this ordered structure. Thus, the latent heat of fusion of a material tends to be one to two orders of magnitude larger than its specific heat. During a phase change such as melting, energy being absorbed by the material is driving the change of phase, instead of increasing the average movement of its atoms or molecules. As such, when a material is changing phase, it maintains a reasonably consistent temperature until the phase change is complete.

In one embodiment, Polyethylene Glycol (PEG) is used as the phase change material and is encapsulated in sealed container 136 comprising a HDPE jar with a polypropylene lid. PEG is chosen as the phase change material 134 due to its high latent heat of fusion, a melting point that is optimal for maintaining the temperature of the thermal reservoir, being a material that is readily available, cost effective, and having been well established as nontoxic. PEG also has the advantage that its melting point can be tuned within a desired range by using various molecular weights of the substance (such as PEG 400 .vs. PEG 600), or by taking its various forms and making aqueous solutions of varying concentrations.

The phase change material 134 could be nearly any material or mixture of materials that achieve the desired melting point and have a suitable latent heat of fusion. Other potential materials include various polymers, oils or mixtures of oils (such as coconut oil), aqueous solutions of polymers or oils, colloidal solutions, nanoparticle solutions, Dimethyl Sulfoxide, acetic acid, or any other materials with a phase change that occurs in the desired temperature range. The main characteristics that form an ideal phase change material are high specific heat, high latent heat of fusion, a melting point in the desired range, and lack of toxicity. With regards to PEG 400 and PEG 600, both have a melting point above that of water.

Figure 7:
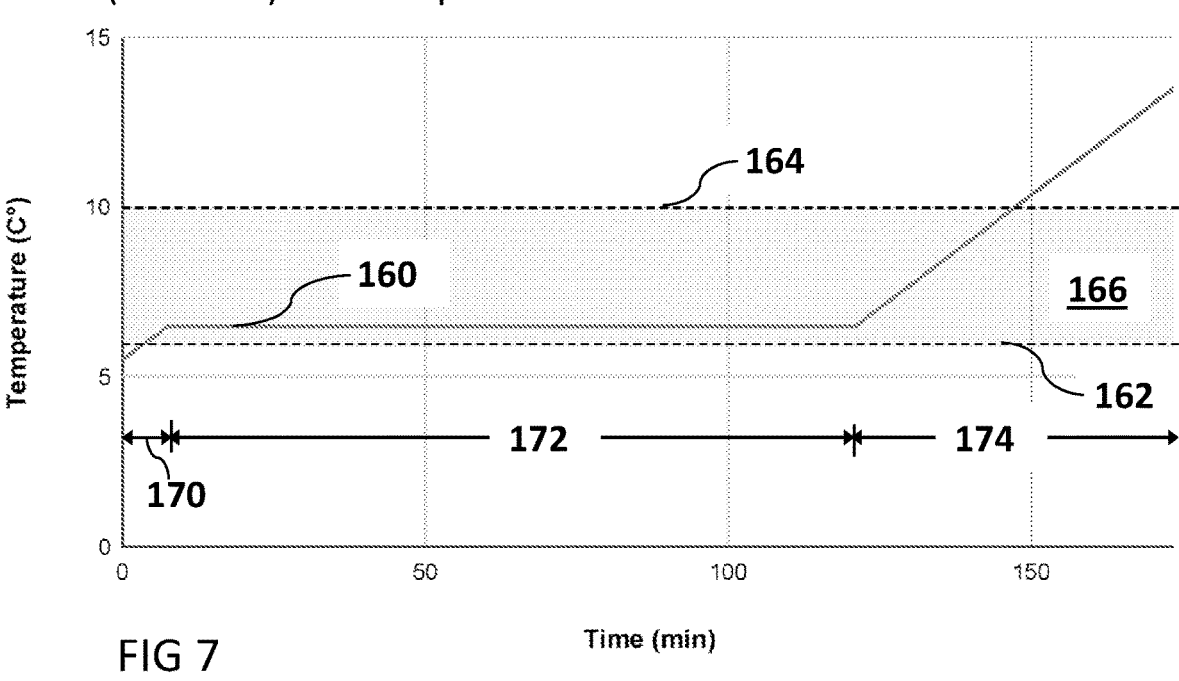
FIG. 7 shows the temperature inside the reservoir over time given a heated stimulus corresponding to an embodiment of the present disclosure.

To illustrate the efficacy of using PEG as a phase change material to maintain the optimum conditions for palm cooling, a specific example with reasonable assumptions is presented in FIG. 7. Initial assumptions of the system are presented herein. First, experimental data has shown that that there is approximately a 5° C. (9° F.) difference between the temperature of the upper heat pipe surface external to the reservoir, and the temperature of the working fluid within the reservoir. To maintain the ideal temperature range for palm cooling, which is approximately 11°-15° C., the reservoir needs to be at a temperature in the range of 6°-10° C. For our system, we determine that there are 350 grams of water and 325 grams of PEG 400 encapsulated in a sealed container. Lastly, we will assume the thermal properties of the encapsulating container are negligible.

The material characteristics necessary to complete the calculation for the temperature within the reservoir are presented herein. The 325 grams of PEG 400 have specific heat of ~2.4 J/g K, the heat of fusion is ~105 J/g, and the melting temperature is 6.6° C. The 350 grams of water have a specific heat of 4.184 J/g C and is already in liquid form.

For this example, the initial equilibrated temperature within the reservoir starts at an equilibrated temperature of 5.5° C., which is slightly below the melting point of PEG 400. For simplicity, we also assume that the power input coming into the reservoir via the heat pipe is continuous and around 5 Watts (or 5 Joules per second). Although in actual use the power input while in contact with the device might be higher, the device would only be held intermittently during a workout or competition, so 5 Watts is a reasonable average power input.

Given the above conditions the graph presented in FIG. 7 shows the temperature changes inside the reservoir over time. As discussed, for efficient palm cooling there is a lower temperature boundary 162 which is required to prevent vasoconstriction, and an upper temperature boundary 164 at which the heat exchanger is no longer effective. The ideal temperature range 166 for the reservoir that maintains the external surface of the heat pipes in the optimal temperature range for palm cooling therefore lies between the lower and upper boundaries.

Figure 8:
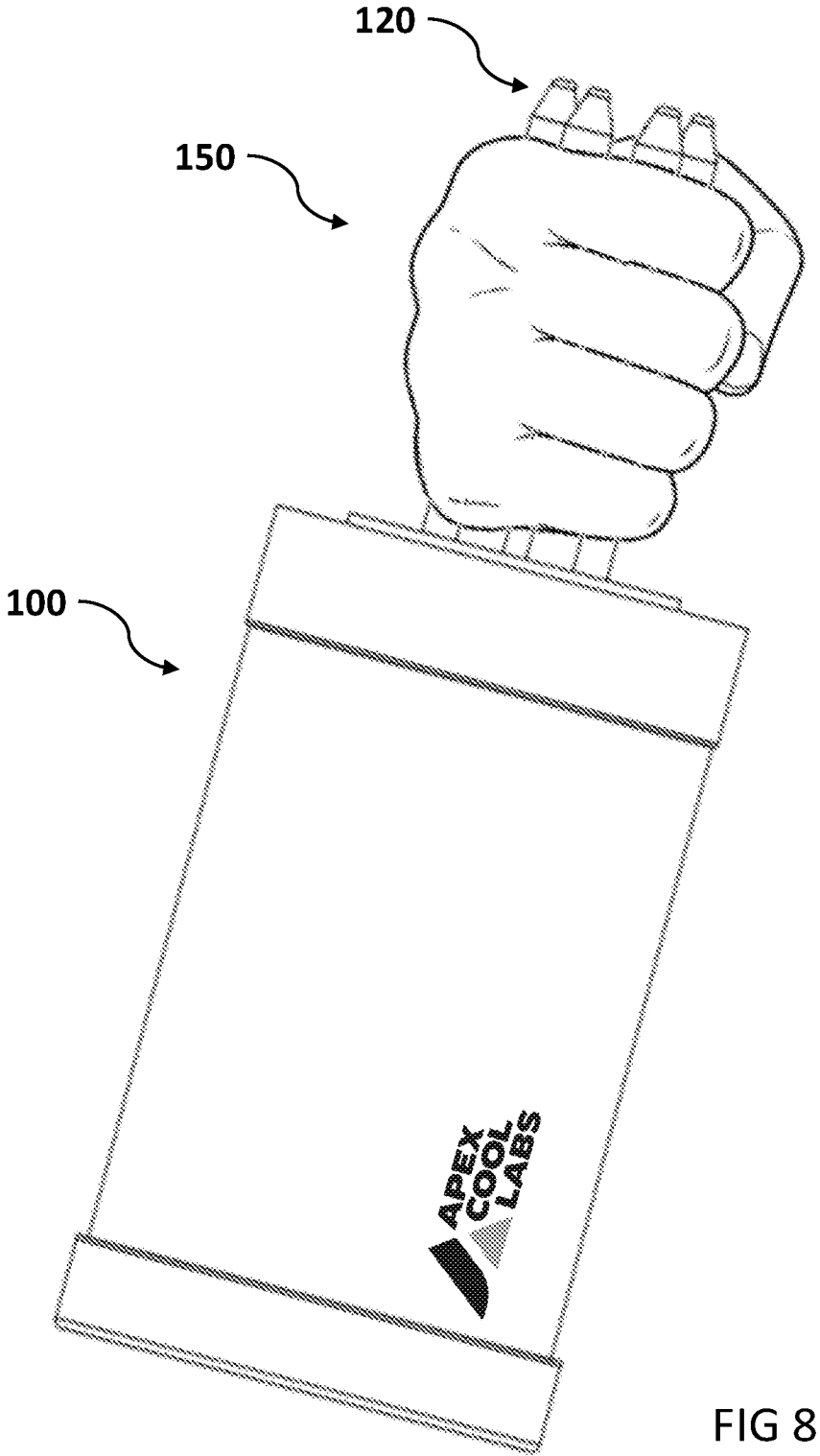
FIG. 8 shows the handheld cooling device in contact with glabrous tissue in the palm of a user corresponding to an embodiment of the present disclosure.

As FIG. 8 illustrates, at first, the temperature 160 rises steadily until the melting point of PEG 400 is reached [time period 170]. Then, as the power input goes into the heat necessary to melt the PEG 400, and during that time the temperature remains constant [time period 172]. Once the PEG 400 has fully melted, the temperature of the water and encapsulated PEG 400 begin to steadily rise [time period 174].

Across time period 172, the reservoir remains within the ideal temperature band for well over 120 minutes (2 hours). The main factor in maintaining proper temperature is the contribution of the phase change from solid to liquid of PEG 400 occurring at a melting point within the ideal temperature range for the reservoir. In real world tests, the device easily maintains its temperature for over 2 hours, with intermittent use, even at warm ambient temperatures, such as above 27° C. (80° F.).

Method of Use

The portable palm cooling device in the preferred embodiment is used to cool the glabrous tissue of the palms as shown in FIG. 8. This cooling is accomplished by: first, placing frozen encapsulated phase change material into the reservoir of the vessel; second, filling the majority of the remaining volume of the vessel with the working fluid; third, securing the lid on the vessel by mating the connectors of the flange lid and vessel flange such that the lower heat pipes are in contact with the working solution; lastly grasping the upper pipes of the device with the palms of the hands so that the upper pipes are in contact with the glabrous tissue.

In the second step of the method above, the temperature of the working fluid at the point of filling is ideally chosen in a range such that when the working fluid and frozen phase change material reach equilibrium, the phase change material is brought to a temperature just below or at its melting temperature. Thus, when the heat exchanger is in contact with glabrous tissue, such as held in the palms of the hands, the heat exchanged to the device is transferred to the act of melting the phase change material, but not changing the temperature of the thermal reservoir.

In the current embodiment, the device is designed to maintain the surface of the heat pipes that will be in contact with the skin at a temperature that will avoid vasoconstriction of the skin but cool enough for efficient thermal exchange (around 55 degrees F.).

ALTERNATE EMBODIMENTS

Figure 9:
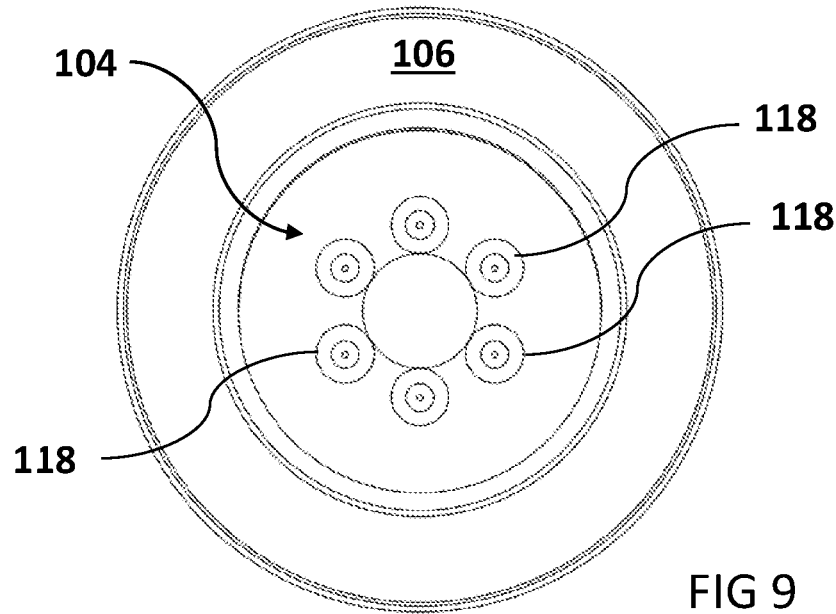
FIG. 9 shows a top view of the heat exchanger arrangement of the handheld cooling device corresponding to an embodiment of the present disclosure.

FIG. 9 shows a top down view of the lid 106 and provides additional details of the heat exchanger assembly 104. Here, the preferred embodiment comprises six heat pipes 118 configured in a hexagon configuration around a central axis. As previously stated, additional or fewer heat pipes can be used to accomplish the same function with various functional and cost tradeoffs.

Figure 10:
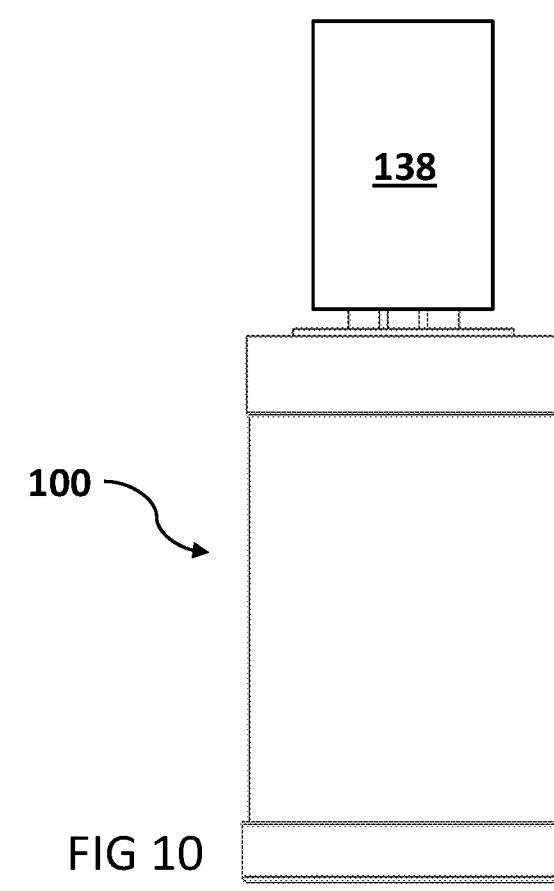
FIG. 10 illustrates the handheld cooling device with an insulated cap corresponding to an embodiment of the present disclosure.

FIG. 10 shows an insulated cap 138 placed over the upper heat pipes. This configuration allows for the device to exist in standby mode for prolonged periods by providing thermal isolation from the environment—as well as mechanical protection.

Figures 11, 12:
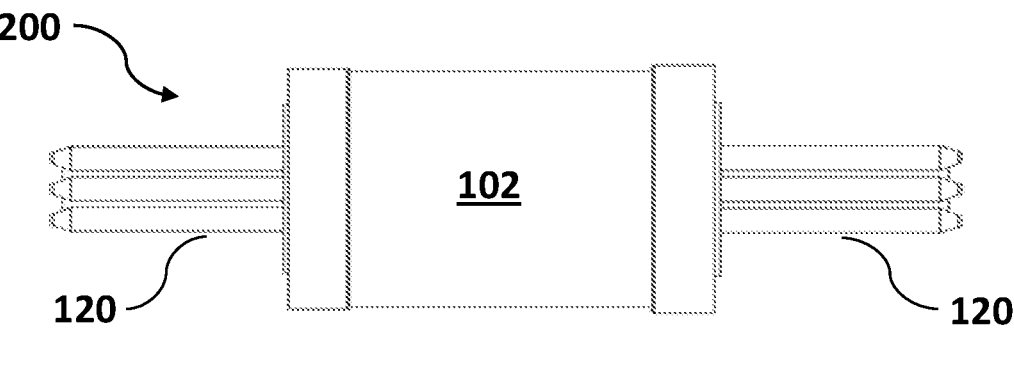
FIG. 11 shows a dual-ended arrangement of the handheld cooling device to facilitate both hands of a user corresponding to an embodiment of the present disclosure.
FIG. 12 shows an additional arrangement of the handheld cooling device to facilitate both hands of a user corresponding to an embodiment of the present disclosure.

FIG. 11 shows an alternative embodiment using principals presented herein to accommodate both hands of a user simultaneously, wherein the upper pipes 120 of the heat pipes extend axially from a reservoir located with a central vessel.

FIG. 12 shows yet another alternative embodiment using principals presented herein to accommodate both hands of a user simultaneously, wherein the upper pipes 120 of the heat pipes extend radially from a reservoir located with a central vessel.

Figure 13:
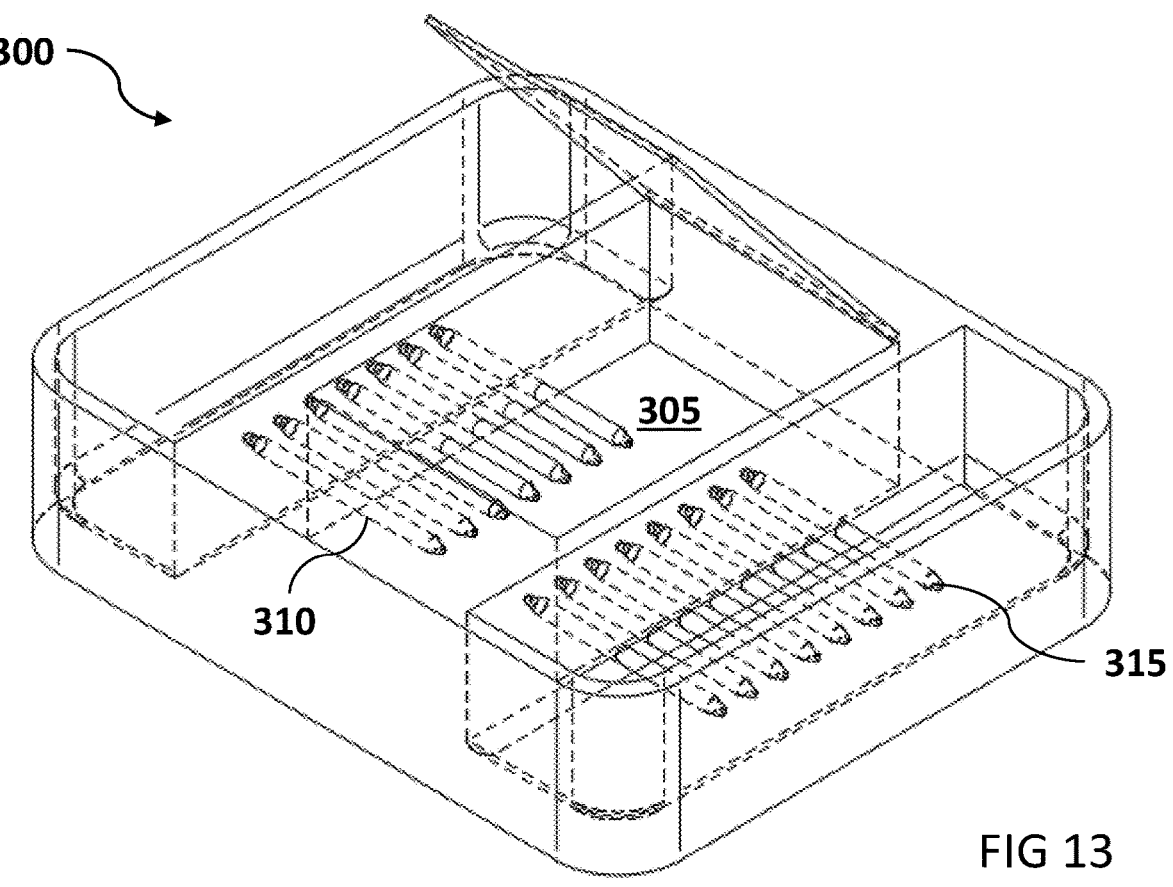
FIG. 13 shows a transparent view of a foot cooling device corresponding to an embodiment of the present disclosure.
Figure 14:
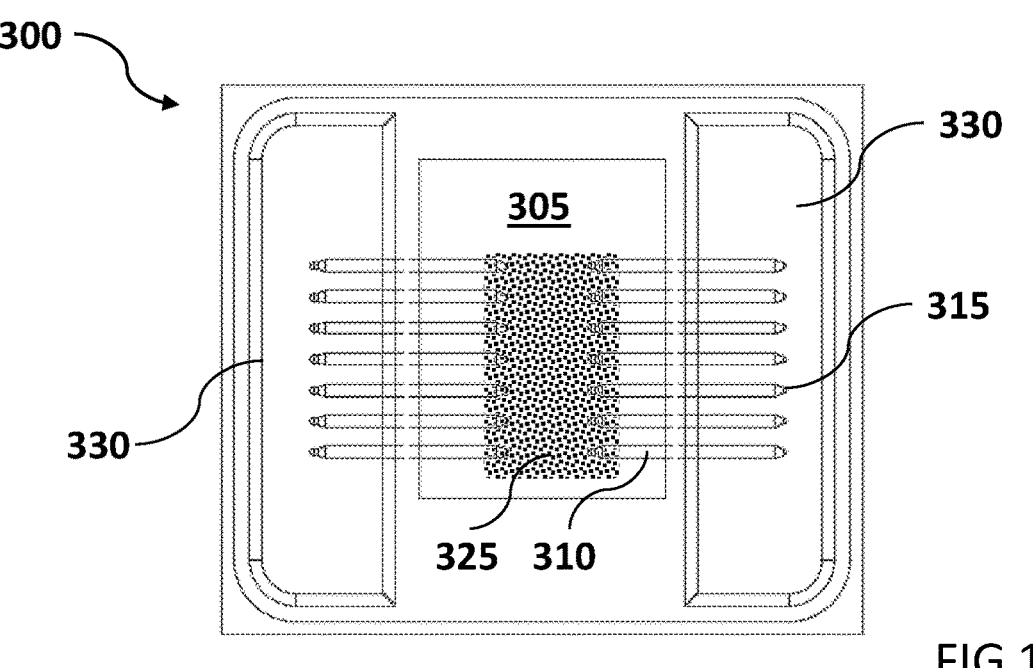
FIG. 14 shows a top view of the foot cooling device corresponding to an embodiment of the present disclosure.

FIG. 13 and FIG. 14 show how concepts presented herein can be applied to glabrous tissue in the feet. As shown, a reservoir area 305 is filled with working fluid 325. The working fluid is in contact with an anterior section of heat pipe 310 within the reservoir. The heat pipe traverses to an exterior section 330 wherein the user may place their feet to enable contact with the external section of heat pipe 315.

What is claimed is:

1. A cooling device for reducing the temperature of a user through contact with glabrous tissue comprising:
   a vessel having an exterior surface and an interior cavity, wherein a vessel wall exists between the interior cavity and the exterior surface, and said interior cavity is fully enclosed and capable of holding a fluid;
      wherein the vessel has a port passing between the external surface and the interior cavity, said port having a lid which operates between an open state and a closed state, wherein the lid in the open state allows the interior cavity to be externally filled with a fluid, and wherein the lid in the closed state seals the interior cavity;
   at least one heat pipe which traverses through the vessel wall,
      said heat pipe having a proximal end and a distal end, wherein the proximal end of the heat pipe resides within the interior cavity of the vessel, and a section of the heat pipe towards the distal end extends a length beyond the external surface of the vessel;
      wherein the section of the heat pipe extending beyond the external surface of the vessel is configured to be in contact with the glabrous skin of the user; and
   a phase change material occupies a space within a sealed container, wherein the sealed container is configured to reside within the interior cavity of the vessel.

2. The cooling device of claim 1, wherein the phase change material comprises polyethylene glycol.

3. The cooling device of claim 2, wherein the phase change material is selected from the group consisting of PEG 400, PEG 600.

4. The cooling device of claim 1 wherein the phase change material comprises a material having a melting point greater than water.

5. The cooling device of claim 2, wherein a plurality of heat pipes are arranged such that each heat pipe resides within the inner cavity and extends beyond the external surface of the vessel.

6. The cooling device of claim 5, wherein exactly six heat pipes are positioned in a hexagonal arrangement.

7. The cooling device of claim 6, wherein a central insulator resides between sections of the heat pipes extending beyond the external surface of the vessel.

8. The cooling device of claim 5, wherein the length of heat pipes extending beyond the external surface of the vessel is between three and six inches.

9. The cooling device of claim 1 wherein said heat pipe consists of a single metal.

10. A cooling device for reducing the temperature of a user through contact with glabrous tissue comprising:
   a vessel having an enclosed inner cavity and an exterior surface;
   a mixture residing within the inner cavity comprising a working fluid and secondary element;
   a heat pipe having a proximal end and a distal end, wherein the proximal end of the heat pipe is in contact with the working fluid, and a section of the heat pipe towards the distal end extends a length beyond the external surface of the vessel; and
   wherein the secondary element is an alternate phase of the working fluid.

11. A cooling device for reducing the temperature of a user through contact with glabrous tissue comprising:

a vessel having an enclosed inner cavity and an exterior surface;

a mixture residing within the inner cavity comprising a working fluid and secondary element;

a heat pipe having a proximal end and a distal end, wherein the proximal end of the heat pipe is in contact with the working fluid, and a section of the heat pipe towards the distal end extends a length beyond the external surface of the vessel; and wherein the secondary element has a melting point higher than the working fluid.

12. A cooling device for reducing the temperature of a user through contact with glabrous tissue comprising:

a vessel having an enclosed inner cavity and an exterior surface;

a mixture residing within the inner cavity comprising a working fluid and secondary element;

a heat pipe having a proximal end and a distal end, wherein the proximal end of the heat pipe is in contact with the working fluid, and a section of the heat pipe towards the distal end extends a length beyond the external surface of the vessel; and wherein the secondary element comprises polyethylene glycol.

13. The cooling device of claim 12, wherein the working fluid is water.

14. The cooling device of claim 12, wherein the working fluid is air.

15. A cooling device for reducing the temperature of a user through contact with glabrous tissue comprising:

a vessel having an enclosed inner cavity and an exterior surface;

a mixture residing within the inner cavity comprising a working fluid and secondary element;

a heat pipe having a proximal end and a distal end, wherein the proximal end of the heat pipe is in contact with the working fluid, and a section of the heat pipe towards the distal end extends a length beyond the external surface of the vessel; and wherein the vessel further comprises a port which passes between the external surface and the interior cavity, said port having a lid which operates between an open state and a closed state, wherein the lid in the open state allows the interior cavity to be filled with the mixture, and the wherein the lid in the closed state forms a watertight seal of the interior cavity.

* * * * *